US006350589B1

(12) United States Patent
Morris et al.

(10) Patent No.: US 6,350,589 B1
(45) Date of Patent: Feb. 26, 2002

(54) COMPOSITIONS OF HIGHLY-PURIFIED NATURAL MIXTURES OF TYPE I INTERFERON DERIVED FROM LEUKOCYTES AND METHODS

(75) Inventors: Joseph P. Morris, Arnold, MD (US); Duy Nguyen, Madison, WI (US); James Kappelman, Worcester; Michael D. Potter, Acton, both of MA (US); Mead M. McCabe, Miami; Reza Ziai, Weston, both of FL (US); Stephen B. Feldman, Passaic, NJ (US); Hipolito Hartman, Miami, FL (US)

(73) Assignee: Viragen, Inc., Plantation, FL (US)

( * ) Notice: Subject to any disclaimer, the term of this patent is extended or adjusted under 35 U.S.C. 154(b) by 0 days.

(21) Appl. No.: 09/224,895

(22) Filed: Dec. 31, 1998

(51) Int. Cl.⁷ .............................. C12P 1/00; A01N 1/02; A61K 45/00; A61K 38/21; C07K 16/00
(52) U.S. Cl. ........................... 435/41; 435/2; 424/85.1; 424/85.4; 424/85.6; 424/85.7; 530/412; 530/414; 530/415; 530/416; 530/351; 530/364
(58) Field of Search ................................. 530/351, 364, 530/412, 414, 415, 416, 417; 424/85.1, 85.4, 85.6, 85.7; 435/41, 2

(56) References Cited

U.S. PATENT DOCUMENTS 5,503,828 A * 4/1996 Testa et al. ................. 424/85.7
5,840,502 A * 11/1998 Van Vlasselaer ........... 435/7.21

OTHER PUBLICATIONS

Scopes, Biotechnol Appli. Biochem., 1996, vol. 23, pp. 197–204.*

Yuqing, Y., Xiaoquin, W.; Study on the Production of Human Interferon –2b Expressed in *Escherichia coli*; Chinese Journal of Biotechnology, vol. 12, No. 1, Copyright 1996 by Allerton Press, Inc.

* cited by examiner

*Primary Examiner*—Yvonne Eyler
*Assistant Examiner*—Janet L. Andres
(74) *Attorney, Agent, or Firm*—Sherman & Sherman; Kenneth L. Sherman; James A. Gale

(57) ABSTRACT

This invention relates to methods for isolating highly-purified mixtures of natural type I interferons from white blood cells. The invention also relates to highly-purified mixtures of natural type I interferons which resemble natural type I interferon in that it includes 9 subtypes, i.e., alpha-1, alpha-2, alpha-5, alpha-7, alpha-8, alpha-10, alpha-14, alpha-21 and omega, giving rise to possibly 20 molecular species, including alpha-1a, alpha-1new, alpha-2a, alpha-2b, alpha-2c, alpha-5, alpha-5LG, alpha-7, alpha-8a, alpha-8c, alpha-10a, alpha-14a, alpha14-b, alpha 14-c, alpha-14LG, alpha-21a, alpha-21b, alpha-21c, omega and omega LG.

5 Claims, No Drawings

COMPOSITIONS OF HIGHLY-PURIFIED NATURAL MIXTURES OF TYPE I INTERFERON DERIVED FROM LEUKOCYTES AND METHODS

FIELD OF THE INVENTION

This invention relates to methods for isolating highly-purified mixtures of natural type I interferons from white blood cells, and particularly human white blood cells. The invention also relates to highly-purified mixtures of natural type I interferons which resemble natural type I interferon in that it includes 9 subtypes, i.e., alpha-1, alpha-2, alpha-5, alpha-7, alpha-8, alpha-10, alpha-14, alpha-21 and omega, giving rise to possibly 20 molecular species, including alpha-1a, alpha-1new, alpha-2a, alpha-2b, alpha-2c, alpha-5, alpha-5LG, alpha-7, alpha-8a, alpha-8c, alpha-10a, alpha-14a, alphal 14-b, alpha 14-c, alpha-14LG, alpha-21a, alpha-21b, alpha-21c, omega and omega LG.

BACKGROUND

The interferons are a family of proinflammatory cytokines important in mediating nonspecific host defense. While of critical importance in initiating anti-viral immunity, the family also acts as a potent initiator of cell growth and differentiation. Type I interferon is a designation for a family of related interferons that can include multiple subtypes of alpha interferon, beta interferon, omega interferons, and in some species the related trophoblast tau interferon. The proteins are structurally similar, share common receptors, have common biological activities and may share a common genetic locus.

The type I interferons are believed to have three major functions. First, they inhibit viral replication by activating cellular genes that inhibit protein synthesis, thus contributing to the suppression of viral replication. Second, they downregulate the proliferation of specific cell types, a characteristic applied to the treatment of certain cancers. Finally, they have an immunomodulatory effect, which can influence the nature of the immune response (i.e. cellular or humoral) while activating innate components such as NK cells or monocytes.

The plurality of effector functions of type I interferons create a variety of potential pharmacological applications. While recognized for their antiviral capability, interferons are also effective in the treatment of some bacterial and eukaryotic pathogens. In addition, the immunomodulatory properties of the group have proven useful in the treatment of some cancers and autoimmune disorders. The literature describing the uses of interferon preparations is vast and includes the use of type I interferons in the treatment of cancers, including leukemias (U.S. Pat. No. 5,830,455), basal cell carcinomas (U.S. Pat. No. 5,028,422), squamous cell carcinomas (5,256,410), breast cancer (U.S. Pat. No. 5,024,833), gastrointestinal malignancies (U.S. Pat. Nos. 5,444,064; 5,814,640), actinic keratoses (U.S. Pat. No. 5,002,764), as well as macular degeneration (U.S. Pat. No. 5,632,984), autoimmune disorders (5,830,456), diabetes (WO09806431A2), bacterial infections (U.S. Pat. No. 5,817, 307), and viral infections (U.S. Pat. No.5,830,456), including genital warts (U.S. Pat No. 4,959,210), hepatitis B (WO09823285A1), and herpes zoster and psoriasis (U.S. Pat. No. 4,957,734). While the pharmaceutical applications of this family of cytokines is only beginning to be understood, the problems related to obtaining an inexpensive and highly purified preparation containing a comprehensive spectrum of type I interferons have limited the therapeutic potential of type I interferon.

A number of different techniques have been utilized to produce quantities of interferons. The successful cloning and sequencing of genes encoding various members of the family have allowed for the recombinant production of individual type I interferon subtypes. While it is possible to produce individual recombinant type I subtypes, these individual recombinant products are limited because (1) their structures may vary from the natural state, and (2) their individual activities may lack the therapeutic potential of all subtypes collectively. Further, individual interferon subtypes cause negative host reactions, including fever, nausea, tissue necrosis and psychopharmacological effects. These side effects have in some cases limited the efficacy of interferon treatment.

Natural interferon production has traditionally involved ammonium chloride treatment of buffy coats to lyse the red blood cells and to isolate the leukocytes, followed by viral stimulation of leukocytes with subsequent large scale harvesting of culture medium. The interferons are then isolated by various precipitation, adsorption, or immuno-affinity techniques.

Despite the use of a variety of purification techniques, the quality, quantity and subtype diversity of the interferons obtained using these methods has remained unsatisfactory. These techniques have generally required tremendous quantities of culture media with processing resulting in a low yield of a product having limited subtype distribution. It is presently believed that the methods described heretofore are unable to achieve easily and economically a sufficiently high recovery rate with a high degree of purity, full functional activity and a full spectrum of natural interferon subtypes. Even immuno-based purification techniques have not produced a full spectrum of type I interferon subtypes because the various subtypes differ in their antigenicity.

One important reason for the low yield of type I interferon from the prior art technicques has been ineffective methods of leukocyte collection, transport, separation, culture and stimulation to secrete interferons. For example, transport mechanisms for whole blood or buffy coats are not optimal for retaining active leukocyte cells, being subject to a wide range of temperatures, high osmolarity, low oxygenation levels and variable transport times. Also, it is believed that lysis of red blood cells with ammonium chloride can greatly reduce the yield of leukocytes, many of which may also be lysed. The remaining leukocytes are osmotically shocked and less effective in their protein synthesis, further reducing the yield of product. Further, the prior art usually employs serum in the culture of leukocytes, which significantly contributes to the resulting contamination of the secreted protein product. The use of viral preparations to induce interferon production also adds a significant source of contaminating material. The prior art has heretofore not addressed these problems.

U.S. Pat. No. 5,503,828 describes an alpha-interferon composition characterized by having at least 50% of alleles of α2 and α8, and one or more additional alpha interferon species selected from the group consisting of α4, α7, α10, α16, α17, and α21. While U.S. Pat. No. 4,503,035 teaches a preparation of certain interferon species, the preparation does not include, for example, alpha-1, alpha-5, alpha-14 and omega subtypes. Thus, a natural mixture of highly pure interferon having a full spectrum of subtypes is not taught by this U.S. Pat. No. 4,503,035.

U.S. Pat. No. 5,762,923 teaches an aqueous interferon composition dissolved in water with a non-ionic detergent and benzyl alcohol in amounts sufficient to stabilize the interferon-alpha. The composition also contains an acidic buffer which provides a pH of 4.5 to 6.0, and may also contain an isotonizing agent. U.S. Pat. No. 4,847,079 teaches a stable pharmaceutical composition of interferon and thimerosal which is resistant to microorganism contamination and growth. U.S. Pat. No. 4,675,184 teaches a stabilized interferon with 15 to 60% by weight of a tri or higher polyhydric sugar alcohol and an organic acid buffer as stabilizers, and a conventional pharmaceutical carrier or diluent at pH about 3 to 6. Optionally, the composition can further contain an anionic surfactant and/or albumin as a stabilizer. U.S. Pat. No. 5,236,707 teaches the use of amine stabilizing agents such as primary aliphatic amines and anionic stabilizing agents such as lithium organo sulfates which protect human interferons from degradation and provide enhanced storage stability. Similarly, U.S. Pat. No. 5,431,909 teaches the use of amine stabilizing agents such as primary aliphatic amines and anionic stabilizing agents such as lithium organo sulfates to protect human interferons from degradation and provide enhanced storage stability.

U.S. Pat. No. 4,780,413 relates to the production of interferon by adding an inducer to lymphoblastoid cells. U.S. Pat. No. 4,172,071 relates to a process for the purification of interferon by absorption onto cliromophore blue columns and elution with a low salt buffer. U.S. Pat. No. 4,289,689 combines affinity chromatography with high pressure liquid clromatography to purify interferons from fibroblasts. U.S. Pat. No. 4,465,622 describes a method of adsorbing interferon onto a carrier containing acrylonitrile polymer and eluting the adsorbed interferon with an appropriate buffer. U.S. Pat. No. 4,485,017 discloses a process wherein a partially purified preparation is passed through an antibody affinity column and a reversed-phase high performance liquid chromatographic column. Organic solvents used during the elution are extracted and the protein concentrated for subsequent use. U.S. Pat. No. 4,551,271 describes the purification of solutions of recombinant interferons by chromatography on metal chelate resins, including copper or nickel. U.S. Pat. No. 5,391,713 describes a process for purification of human leukocyte interferon which includes immunoaffinity chromatography, ion-exchange chromatography, and a series of precipitation and centrifligation steps.

While these disclosures provide different methods for obtaining an interferon preparation, they fail to provide a naturally-occurring interferon product derived from white blood cells which has full subtype distribution, and as a result, have limited yield and utility. Moreover, these processes can be inefficient and quite expensive.

Consequently, there is a need for a highly-purified preparation of interferon that resembles natural type I interferon which contains a full spectrum of interferon subtypes, which is substantially free of contaminating proteins, and which is particularly applicable to therapeutic uses, and for a process for obtaining in high yields such a highly-purified preparation of interferon. Moreover, such a process should be simple and efficient so that it remedies the inconveniences faced with interferon purification procedures available heretofore.

SUMMARY OF THE INVENTION

In brief, the present invention alleviates and overcomes certain of the above-identified problems and shortcomings of the present state of interferons through the discovery of novel highly purified mixtures of Type I interferon derived from white blood cells, and novel methods of isolating and using same.

The multisubtype Type I interferons of the present invention are a highly purified blend of natural $\alpha$ and $\omega$ interferons obtained from leukocytes. The leukocytes may be derived from blood or a blood component, such as an apherisis product. It is believed that no proteins, other than interferon proteins, can be detected in the multisubtype Type I interferons of the present invention using standard gel elctrophoresis techniques. Moreover, the multisubtype Type I interferons of the present invention do not contain any nucleic acids. It is believed that the multisubtype Type I interferons of the present invention achieve a purity of at least about 95%, and up to about 98%. In other words, the multisubtype Type I interferons of the present invention are virtually free of contaminants, such as serum albumin and other low and high molecular weight proteins. The molecular weights of the multisubtype Type I interferons of the present invention are generally between about 10,000 and about 30,000 Daltons, and more particularly between about 19,000 and 27,000 Daltons, as measured by SDS-Page. The multisubtype Type I interferons of the present invention have an activity of at least about $1 \times 10^8$ units, as measured by a standard anti-viral assay conatining an international interferon standard, and apparent isoelectric points of between about 5.0 and about 8.5. Still further, the multisubtype Type I interferons of the present invention include both naturally glycosylated and naturally unglycosylated forms of interferon subtypes. The naturally glycosylated subtypes are believed to include alpha-2 species, alpha-14 species, alpha-21a and omega.

Uniquely, the multisubtype Type I interferons of the present invention resembles natural Type I interferon and in particular, natural human Type I interferon in that it contains a mixture of multiple IFN-$\alpha$ and IFN-$\omega$ subtypes derived from white blood cells. More specifically, there are believed to be at least 9 different subtypes that can give rise to at least 16, and possibly 19 or more molecular species. The 9 subtypes include alpha-1, alpha-2, alpha-5, alpha-7, alpha-8, alpha-10, alpha-14, alpha-21 and omega, whereas the 19 molecular species include alpha-1a, alpha-1new, alpha-2a, alpha-2b, alpha-2c, alpha-5, alpha-5LG, alpha-7, alpha-8a, alpha-8c, alpha-10a, alpha-14a, alphal14-b, alpha 14-c, alpha-14LG, alpha-21a, alpha-21b, omega and omega LG. Because the multisubtype Type I interferons of the present invention contain a plurality or a significant number of different Type I interferon subtypes, it is believed that the multisubtype Type I interferons of the present invention very closely resemble the natural Type I interferon system and, in particular, the natural human Type I interferon system produced by and operating within humans, especially when compared to the recombinant monocomponent interferon products available heretofore.

The present invention also contemplates novel procedures for obtaining the multisubtype Type I interferons. For example, the present invention is concerned with methods of obtaining a highly purified mixture of Type I interferon having a plurality of subtypes from leukocytes wherein the highly purified mixture of Type I interferon has a purity of at least about 95%, contains substantially only interferon proteins, contains at least 9 different subtypes, including alpha-1, alpha-2, alpha-5, alpha-7, alpha-8, alpha-10, alpha-14, alpha-21 and omega which gives rise to at least 16 and possibly 19 or more molecular species, and contains no more than about 35% by weight IFN$\alpha$-2 and IFN $\alpha$-8 subtypes. Such a method comprises: (a) culturing leukocytes; (b) stimulating the leukocytes to produce a crude interferon; (c) concentrating the crude interferon to remove low-molecular weight contaminants; (d) liquid volume to produce a concentrated crude interferon; (e) removing a substantial amount of serum albumin and other contaminants from the concentrated crude interferon to produce a partially purified interferon mixture containing a plurality of subtypes; (f) removing substantially all remaining serum albumin and other contaminants from the partially purified interferon mixture to generate an interferon mixture having a purity of between about 50% and about 80%; and (g) purifying the about 50% to about 80% interferon mixture to produce a highly purified mixture of Type I interferon having a purity of at least about 95% and containing no more than about 35% by weight IFNα-2 and IFN α-8 subtypes.

Such a method may include the further step of isolating the leukocytes from blood or a blood component, such as an apheresis product.

Turning now to the novel procedures for obtaining the multisubtype Type I interferons of the present invention from leukocytes, they generally involve four segments: (1) leukocyte acquisition; (2) isolation of peripheral blood mononuclear cells (PBMC); (3) cell culture and interferon production in cell culture; and (4) purification of multisubtype Type I interferon.

Generally speaking, there are numerous advantages associated with these four segments. For instance, the acquisition of leukocyte segiment results in an increase in the number of leukocytes due to better component manufacturing procedures. Additionally, the leukocytes are generally more hardy and have increased productivity due to the handling and isolation procedures. Moreover, there is improved productivity of a "unit" of leukocytes due to improved recovery from each donation, increased productivity due to additives added at the "buffy coat" stage and temperature maintenance procedures. The additives into the buffy coat are believed to improve white blood cell health and separation. Notwithstanding, it should be appreciated that the procedure of the present invention is time sensitive from the nature of the donation to component manufacture to the PMBC isolation segment to IFN production. In addition, the procedures of the present invention requires the use of gas permeable bags during storage of the harvested white blood cells and temperature maintenance (ambient, RT) during all steps leading from 1 donation to culture.

As to the PBMC isolation segment, the PBMCs are generally healthier because the procedures of the present invention gently remove red blood cells from the white blood cells without lysis, the PMBCs are maintained at physiological ionic strength throughout the PBMC isolation process, the white blood cells are gently washed, and the PBMCs are gently isolated via use of LSM at manufacturing scale. Moreover, because plasma and plasma proteins are removed, the use of non-immunoaffinity purification procedures can be used downstream to attain a purity of greater than about 95%. Finally, because the PBMCs are isolated, this limits proteolysis in cell culture.

During the cell culture and IFN production in cell culture segment, plymorphonuclear leukocytes (PMNs) are removed to minimize the adverse effects of protease. Further, use of purified Sendai Virus in cell culture and protein free medium enhances purification, limits the need for immunoaffinity, and removes any non-human proteins from the system. To enhance the benefit of this segment, protease inhibitors should be used during cell culture and suicide inhibitors of protease activity should be used immediately after cell culture to prevent product proteolysis. Moreover, pH, temperature, $pO_2$, prevention of PMN breakdown, and cell health should be controlled during cell culture. Also, monocytes in the cell culture and presence of an inducing factor during the first two hours of cell culture after Sendai addition are generally needed.

With respect to the segment concerning purification of the multisubtype Type I interferon, the protein burden of all steps leading to purification is reduced so that non-immunoaffinity and non-RP-HPLC methods can be effectively employed for purification. This benefit reduces costs, limits structure degradation and enhances the full recovery of Type I interferon subtypes. A reduction in protein burden suring this segment is accomplished by using protein free cell culture medium, purified Sendai, extensive washing of isolated white blood cells and removal of PMNs to prevent the release of their cellular contents into the purification stream. Moreover, this benefit provides for the capture of a multisubtype Type I interferon which contains a mixture of multiple INF-α and INF-ω subtypes derived from white blood cells. This is believed to be particularly advantageous in view of the strong anti-viral activity noted for INF-ω subtypes.

DETAILED DESCRIPTION OF THE INVENTION

By way of illustrating and providing a more complete appreciation of the present invention and many of the attendant advantages thereof, the following detailed description and examples are given concerning the novel highly purified mixtures of Type I interferons derived from white blood cells in the present invention, and novel methods of isolating and using same.

Definitions and Abbreviations

In connection with the present invention, the following terms shall have the following meanings.

BC—Buffy coat.

BCA—Assay used for protein concentration determination.

Capture pool—concentrated interferon prepared from a culture medium by, for example, Sepharose Big Bead chromatography.

Crude interferon—Any sample of type I interferon that is less than 35% pure, including the culture media into which interferon is secreted and concentrated culture medium.

CV—column volume.

ELISA—Enzyme linked Immunosorbent Assay. Commercial ELISA kits for detecting various interferons are used herein.

HEPES—N-2-Hydroxyethylpiperazine-N'-2-ethanesulfonic acid.

Natural Mixture of Type I IFN or Interferon—Natural mixture of type I IFN or interferon, or any similar phrase, refers to any natural type I interferon obtained from white blood cells which comprises a blend of nine sub-types, i.e., α1, α2, α5, α7, α8, α10, α14, α21, and ω), giving rise to at least 16, and possibly 20 or more, different molecular species, including alpha-1a, alpha-1new, alpha-2a, alpha-2b, alpha-2c, alpha-5, alpha-5LG, alpha-7, alpha-8a, alpha-8c, alpha-10a, alpha-14a, alpha-14-b, alpha 14-c, alpha-14LG, alpha-21a, alpha-21b, alpha-21c, omega, omega LG and/or others.

LSM®—Lymphocyte Separation Medium. Contains ficol and hypaque.

MES—2-(N-Morpholino)ethanesulphonic acid.

PBS—phosphate buffered saline.

PBMC—peripheral blood mononuclear cells.

Pefabloc®—A commercially available serine protease inhibitor or its equivalent. Also, Pefabloc SC®

Percoll®—A commercially available solution of low osmolarity (<25 mOsm/kg $H_2O$) with variously sized silica particles. Any equivalent may be used PF68—Pluronic acid F-68.

RB-1—refined buffy coat. Prepared by washing crude buffy coats with PBS (see example 2).

RP-HPLC—Reversed phase high performance liquid chromatography.

RPMI—Nutrient medium that supports leukocyte culture.

Semi-permeable bag—Also semi-permeable container. Any container with a large surface area to volume ratio that allows gas to pass through the container walls.

Serum-free culture medium—any culture medium that can be used to support the growth of leukocytes and their production of interferon, but that does not contain any fetal calf or other type of serum. This includes at least RPMI, and MEM as well as others known to those of skill nt the art.

Tris—N-Tris(hydroxymethyl)aminomethane.

VSV—vesicular stomatitis virus. Used in a bioassay to assess interferon anti-viral activity.

One aspect of the current invention concerns a highly purified mixture of Type I interferons containing at least 9 subtypes which gives rise to at least 16, and possibly up to 20 or more, molecular species. The 9 subtypes include IFN-α1, IFN-α2IFN-α5, IFN-α7, IFN-α8, IFN-α10, IFN-α14, IFN-α21 and IFN-ω. The molecular species include IFN-(α1a, IFN-α1new, IFN-α2a, IFN-α2b and/or IFN-α2c, IFN-α5, IFN-α5LG, IFN-α7, IFN-α8a, IFN-α8c, IFN-α10a, IFN-α14a and/or IFN-α14b and/or IFN-α14c, IFN-α14LG, IFN-21a and/or IFN-α21b, IFN-α21c, IFN-ω and IFN-ωLG.

It should be appreciated by those versed in this art that the amounts of the subtypes and the individual molecular species in a highly purified natural mixture of Type I interferon obtained in accordance with this invention vary depending upon the method selected to isolate the natural mixture of Type I interferon from the leukocytes. Moreover, while the methods described herein will isolate highly purified natural mixtures of Type I interferon from white blood cells, any method of preparing a natural mixture of interferons with the characteristics described herein will suffice. The term "natural mixture" refers to the fact that the interferons are "native" or "natural", e.g., not recombinant, and that they are purified as a mixture from white blood cells, rather than as individual subspecies which are then recombined.

The subtype listing provided above lists only those subtypes identified to date. Additional sequencing and peptide mapping studies of the highly purified natural mixtures of Type I interferon isolated in accordance with the present invention may determine that subtypes IFN-α7, IFN-α8, IFN-α10, IFN-α14 include the additional subtypes IFN-α7a, IFN-α7b, IFN-α7c, IFN-α8b, IFN-α10b,. Additionally, subtypes IFN-α4a, IFN-α4b, IFN-α16, IFN-α17a, IFN-α17b, IFN-α17c, and IFN-α17d may also be present as suggested by preliminary experiments.

Currently, it is believed that the major subtypes are about 25% IFN-α1 (a and new), about 15% IFN-α2 (a and b and/or c), about 5% IFN-α5 (a and LG), about 5% IFN-α7, about 10% IFN-α8 (a and c), about 10% IFN-α10a, about 10% IFN-α14 (a, b and/or c), about 10% IFN-α21 (a, b and/or c) and about 5% IFN-ω.

The highly purified natural mixtures of Type I interferon are stabilized in a buffer with the addition of about 1 mg/ml HSA. Although most prior ait interferon solutions employ acidic buffers in which to formulate the interferon, it has been found that a neutral pH works best under the conditions described. It should also be understood that the natural mixtures of Type I interferon of the present invention are suitable candidates for standard freeze-drying techniques.

For best results, the interferon is kept in silanized vials at 4° C. and the vials may be sparged with $N_2$ if desired. Any biocompatible buffer can be used to formulate the interferon and additional excipients and/or active ingredients may be added as necessary for the use and/or mode of application.

Because the highly-purified natural mixtures of Type I interferon of the present invention contain a full spectrum of interferon subtypes which are substantially free of contaminating proteins thereby closely resembling the natural interferons produced by humans from leukocytes, they are particularly applicable to therapeutic uses. For example, the present invention contemplates a method of treating interferon-responsive diseases by administering an effective amount of a highly purified natural mixture of Type I interferon (IFN) isolated from white blood cells in accordance with the present invention in a pharmaceutically acceptable carrier, said natural mixture of type I IFN being at least about 95% pure before being combined with said pharmaceutically acceptable carrier, and said natural mixture of type I IFN comprising at least 9 subtypes which gives rise to at least 16, and possibly up to 20 or more, molecular species. The 9 subtypes include IFN-α1, IFN-α2, IFN-α5, IFN-α7, IFN-α8, IFN-α10, IFN-α14, IFN-α21 and IFN-ω. The molecular species include IFN-α1a, IFN-α1new, IFN-α2a, IFN-α2b and/or IFN-α2c, IFN-α5, IFN-α5LG, IFN-α7, IFN-α8a, IFN-α8c, IFN-α10a, IFN-α14a and/or IFN-α14b and/or IFN-α14c, IFN-α14LG, IFN-α21a and/or IFN-α21b, IFN-α21c, IFN-ω and IFN-ωLG.

The methods of the present invention concern those diseases or indications that are interferon-responsive and include, for example, hepatitis infection, such as hepatitis A infection, hepatitis B infection, hepatitis C infection, HIV infection, heipes zoster virus infection; influenza infection, common cold infections, hemorrhagic fever infections, genital warts, bacterial infections, chlamydia infection, Behcet's disease, Churg-Strauss syndrome, leukemia, T-cell leukemia, hairy cell leukemia, chronic myeloid leukemia, melanoma, myofibromatosis, T-cell lymphoma, basal cell carcinomas, squamous cell carcinomas, renal cell carcinoma, colorectal carcinoma, non-small cell lung cancer, cervical cancer, breast cancer, gastrointestinal malignancies, actinic keratoses, macular degeneration, autoimmune disorders, diabetes, psoriasis, multiple sclerosis, inflammatory bowel disease, rheumatoid arthritis, systemic lupus erythematosus and the like.

Consistent with the present invention, the highly purified natural mixtures of type I interferon (IFN), when intimately admixed in a pharmaceutically acceptable carrier, may be administered topically, orally, parenterally, sublingually, buccally, by nasal iinalation, rectally, vaginally, aurally, or ocularly.

Turning now to the general procedure for the preparation and culture of letikocytes according to the present invention, it begins with collecting, transporting and separating leukocytes from other blood cell fractions. Traditionally, leukocytes have been collected as whole blood and stored in impermeable plastic bags at about 4 C to about 25 C temperature until processed into plasma and red blood cells. The white blood cell layer (buffy coat) is generally a discarded side product of the process which can be collected and then treated with ammonium chloride to lyse the contaminating red blood cells. The remained leukocytes are then cultured in media containing a serum such as fetal calf serum and activated with a viral inducer to produce interferon.

In this invention, it has been discovered that it is possible to greatly improve the viability and activity of the white cells by changing this process to maximize and protect them during the collection, transport, purification and the subsequent culturing of leukocytes. Generally, the procedure is as follows:

Whole blood is collected at various collection centers and centrifuged to produce a buffy coat. Collection of the buffy coats is done with a peristaltic pump and a specially designed manifold that is much gentler than a vacuum pump. An initial wash with PBS selves to remove both platelets and some serum contaminants as well. After centrifugation, the supernatant is removed with a peristaltic pump and specially designed aspirators. Then the cells are gradually brought to isotonic osmolarity with PBS washes.

The transport of blood or buffy coats, if necessary, should be done in such a way as to minimize temperature variations, time of transport and maximize the oxygenation of the cells. The use of semi-permeable plastic bags hung from the top of an insulating container so as to allow free flow of oxygen between and into the bags greatly increases the viability of the leukocytes. Further, the temperature should be maintained at 22°±3° C. This has been achieved with the use of water bags inside the insulating container. Of course, the time between collection and processing should be minimized.

Instead of lysing red blood cells with salt, the various cells in the buffy coat are separated by density centrifugation on an LSM™ gradient with Percoll™ overlay with a slightly mixed LSM™/Percoll™ interface. After centrifugation, the second cell layer, containing the PBMC, is recovered with a peristaltic pump, washed in PBS and then transferred into RPMI medium. The use of this procedure minimizes the number of granulocytes, thus reducing the protease contamination of later cultures. Throughout this procedure, it is important that the cells be maintained at a constant room temperature. Even a brief exposure to low temperatures can cause inadequate separation and lowered IFN production.

The PBMC cells are cultured in a serum-free medium, such as RPMI, in order to minimize contaminants throughout the later product purification procedures. For Type I interferon production, the cells are cultured with interferon primer at 37° C. for about 2 hours. Sendai virus is added and the culture continued for another 2 hours. Then the temperature is smoothly and quickly dropped to 28° C. and culture continued for about 14 hours. One half hour before the end of culture, a protease inhibitor can be added, but this step is optional.

The Sendai virus that is used to stimulate interferon production is generally grown in the allantoic fluid of chicken eggs. This provides an additional source of contaminating proteins in the final interferon product. Therefore, in order to maximize product yield and purity, this additional source of contaminants is purified about 1000 fold by centrifugation of the Sendai virus on a potassium tartrate density gradient or by other methods known in the art.

After harvest of the interferon-containing culture media, the contaminating virus can be killed by incubation of the product at pH 2. Virus hemagglutination activity is eliminated in 30 minutes of low pH treatment. Further, interferon activity, as measured by anti-viral bioassay, is not negatively affected by up to 24 hours of acid treatment.

This interferon capture pool is the starting product for the purification procedures discussed hereinafter.

Following the culture of the cells with the appropriate inducer, the supernatant is removed from the cells and initially concentrated 100 fold by cation exchange chromatography. Other means of concentration commonly practiced in the art are envisioned by the present invention, such as salt precipitation, ultrafiltration, dialysis, gel filtration, affinity chromatography, electrofocusing or electrophoresis or a combination of two or more of the above techniques.

The concentrated interferon obtained from leukocyte culture is then purified in three steps as follows.

First, interferon is isolated from the concentrate by hydroxyapatite (HA) chiromatography at a low pH in the range of about 4.9 to about 5.2, and more preferably at about pH 5.0. This removes about 98% of the major contaminant which is human serum albumin, and other contaminating proteins, and provides an approximately 10 fold purification and additional concentration. The partially purified interferon can be further purified by size exclusion chromatography (SEC) to remove the remaining human serum albumin and other minor contaminants. If desired, this is followed by anion exchange (AX) chromatography or hydrophobic interaction chromatography (HIC) or both.

When (1) HA, (2) SEC and (3) AX or HIC or AX and HIC are performed in sequence, a natural interferon mixture is produced that is between about 95% and 98% pure, and has the following characteristics: (a) it contains at least nine interferon subtypes giving rise to at least 16, and possibly 19 or more, molecular species, (b) a mixture of apparent molecular weights of between about 10,000 and about 30,000 Daltons and more particularly between about 19,000 and 27,000 Daltons, as measured by SDS-PAGE, (c) an activity of at least about or greater than $1 \times 10^8$ units, as measured by a standard anti-viral assay containing an international interferon standard, and (d) apparent isoeletric points of between about 5.0 and about 8.5. The natural mixture of type I INF or interferon is thought to include both naturally glycosylated and naturally unglcosylated forms of interferon subtypes. Most subtypes, however, are thought to be unglycosylated. The glycosylated subtypes are believed to include alpha-2 species, alpha-14 species, and omega species.

Further, the subtype characterization to date reveals that the natural mixture of type I interferon comprises:

| | | |
|---|---|---|
| (1) | alpha-1a | |
| | alpha-1new | about 30% (1a and 1new) |
| (2) | alpha-2a | |
| | alpha-2b | about 15% (2a and 2b and/or 2c) |
| | alpha-2c | |
| (3) | alpha-5 | about 5% |
| | alpha-5LG | |
| (4) | alpha-7 | about 5% |
| (5) | alpha-8a | |
| | alpha-8c | about 10% (8a and 8c) |
| (6) | alpha-10a | about 10% |
| (7) | alpha-14a | |
| | alpha-14b | |
| | alpha-14c | |
| | alpha-14LG | about 10% (14a, 14b, 14c and/or 14LG) |
| (8) | alpha-21a | |
| | alpha-21b | about 10% (21a, 21b and/or 21c) |
| | alpha-21c | |
| (9) | omega | about 5% |
| | omega-LG | |
| | Total | About 100% |

Further, when hydrophobic interaction chromatography (HIC) is included as the final purification step without the use of anion exchange, the natural mixture of type I INF or interferon may contain cytokine IL-6 in an amount of about 1/7000 to 1/500 of a clinically relevant therapeutic dose of IL-6.

Comparison with commercially available interferon preparations, such as Wellferon™ (Burroughs-Wellcome), Alferon-n3™ (Interferon Sciences, Inc.), Roferon-2a™ (Roche Laboratories) and Intron-2b™ (Schering-Plough) reveals that these commercial preparations, in contrast, completely lack subtype-omega (as assayed by ELISA (Bender Wein)). Moreover, because these interferon preparations do not contain a full spectrum of subtypes derived directly from white blood cells, it is believed that they cannot resemble the natural type I interferon produced by leukocytes within the body.

It should be understood that when anion exchange is selected as the final step in the procedure in accordance with the present invention (HA, SEC, AX), IL-6 is removed. In addition, the amounts of the subtypes omega, alpha-14 and alpha-21 in the natural mixture of type I INF or interferon are substantially reduced. If the subtype omega is removed, the isoeletric point range changes from between about 5.0 to about 8.5 to between about 4.0 to about 6.0. Of course, the relative ratios of the subtypes in the natural mixture of type I INF or interferon produced by this method are adjusted appropriately by the removal of significant amounts of subtypes omega, alpha-14 and alpha-21.

It should also be understood that when anion exchange and HIC are selected as the final step in the procedure in accordance with the present invention (HA, SEC, AX and HIC), only IL-6 is removed. Again, the relative ratios of the subtypes in the natural mixture of type I INF or interferon produced by this method, i.e., HA, SEC, AX and HIC, are adjusted appropriately by the removal of IL-6.

In order that the invention and its advantages may be more completely understood, the following examples are provided as a means of illustration but are in no way considered as a limitation on the scope of the present invention.

EXAMPLE 1

Transport of Buffy Coats

Whole blood is collected at various collection centers and centrifuged to provide plasma, red blood cells and a buffy coat interface which can be separated and transported to a manufacturing facility. Buffy coat viability is maximized by avoiding a high osmolarity environment and this can be achieved by washed with isotonic PBS or adding an appropriate stabilizer. Buffy coats are transported in an insulating container (such as a Styrofoam cooler) of appropriate size for the number of bags to be transported. Preferably, the container is also packed with two bags containing water (or other fluid) at a temperature of 22°±3° C. in order to maintain the temperature inside the cooler at 22°±3° C. Transport under these conditions provides reproducible interferon titers.

Maximizing the oxygenation of the leukocytes also helps to improve cell viability and interferon titers. To that end, buffy coats (or whole blood, leukocytes, or other cell fraction) are transported in a semi-permeable (gas penneable) bag (or other container) and hung inside the cooler in such a way as to ensure gas flow between the bags. This can be done in a variety of ways. For example, by hanging the bags from a rack, clipping the bags to a rack or by equipping the bags themselves with a hanging means such as a hook (or eyehole) which can be set into an eyehole (or hook) on the lid, or the bag may have a rigid bar on the top edge which can be set into grooves in the cooler. Additional oxygenation can be achieved by sparging the container itself with $O_2$ before transport or using bags with greater $O_2$ permeability.

EXAMPLE 2

Purification of Peripheral Blood Mononuclear Cells from Buffy Coats

Density purification of white blood cells with ficoll-hypaque gradients is widely used in both research and clinical settings. This technique combines an osmotic agent (hypaque) which dehydrates the red blood cells as they pass through the material. A density gradient is formed by the dilution of the ficoll by the water displaced by the red blood cells and present in the plasma. In addition to reducing the red cell volume, this method also causes the red blood cells to aggregate, thus further increasing their apparent density. The commercial preparation LSM™ from Organon-Technica was selected as the reference method for these studies.

Experiments were then conducted at manufacturing scale (400 ml Nalgene polycarbonate centrifuge bottles) to evaluate the ability of Percoll™ solutions of varying densities to improve the LSM™ separation. These included experiments in which the density of cell containing solutions and fractions were determined by the use of hydrometers. These data and several empirical studies, led to the use of a p=1.07 g/ml Percoll™ overlay on the LSM™.

The Percoll™ overlay is thought to work by retarding the entry of the PBMC into the LSM™. The lower resultant granulocyte concentration has the added benefit of reducing the protease content of the cultures, and thereby increasing the interferon yield. An interesting theoretical discussion on the separation of lymphocyte subsets can be found in Hunt, S. V. (1978) Separation of lymphocyte sub-populations. In *Handbook of experimental immunology* (D. M. Weir, ed) Alden Press, Oxford.

While the Percoll™/LSM™ method may limit the exposure of the PBMC to hypaque, it likely does not significantly reduce the potential for toxicity. It is therefore important that the procedure be complete in a timely fashion and the cells be adequately washed following their isolation. Standard laboratory protocol requires that the PBMC layer be washed twice in a 3 fold dilution with PBS following ficoll-hypaque isolation. A single wash in five dilution volumes proved adequate to maintain interferon production. However, a second wash significantly reduces the level of contaminating proteins encountered during further purification steps.

Ficoll-hypaque methods are very sensitive to prior isolation conditions. If the cells, at any time after donation, are subjected even briefly to low temperatures (i.e. 2–8° C.) the separation is inadequate. Likewise if the cells are ever exposed to a growth media, such as RPMI, the separation may fail entirely. After evaluating wash solutions such as HEPES or RPMI, the best results are obtained using PBS for all cell washes, prior to and following the Percoll™/LSM™ separation.

The three PBS washes (one during the RB-1 formation and two after harvesting the principal layer) effectively reduce the osmolarity to approximately 288±2 mOsm. It is discovered that monocyte survival is imperative for maximal natural mixture of type I INF or interferon production and that in contrast, granulocyte degradation leads to the degradation of the interferon. With the techniques described herein, the proportion of monocytes present in the final cell concentrate was consistently over 10%, and generally over 15%. The proportion of granulocytes was consistently under 20%, and generally under 10% and most frequently below 5%.

Specifically, the procedure is as follows: The buffy coats are combined through a manifold via a peristaltic pump through thick silicon tubing (I.D. 5/16" O.D. 9/16" Wall 1/8"). A specially designed manifold has been designed as to permit optimal cell collection rate and ease. The peristaltic pump with manifold is gentler on the cells than a vacuum pump and provides better interferon titers. Care is taken not to introduce air into the system and minimize foaming, which is detrimental to the cells. Clamping the tubing between the manifold and pump while attaching and removing the leukopacs minimizes the introduced air.

Pooled leukocytes are divided into one liter bottles and centrifuged for 20 minutes at 400 G. This removes residual platelets and some serum proteins as well. All centrifuge steps detailed herein are performed with the IEC 7000M Programmable centrifuge or equivalent. Changes to the centrifuge, rotor or bottle may dramatically alter the quality and quantity of cells recovered.

The supernatant plasma is removed by gentle aspiration and a peristaltic pump. Two aspirators are used for this process. One is bent at 90 degree and has a sealed tip and a slot in the upper surface of the short aim of the tube and is useful for separating the layers of supernatants. The tube is lowered just into the lower layer while the upper layer is aspirated. The second aspirator is also bent at a 90 degree angle and has a slightly flattened open tip which is useful for removing cells that adhere to the wall of the container. Currently, the tubes are made with polycarbonate tubing which allows them to be autoclaved without breakage, although other materials may be used. Placing the bottles on a turntable may aid in successful aspiration.

The plasma volume that is removed is replaced with isotonic PBS (290 mOsm) and gently mixed by swirling the bottle. The cells are concentrated by centrifugation for 15 minutes at 800 G (1700 rpm). This forms a refined buffy coat (RB-1) which is collected via peristaltica spiration into a separate flask. Percoll™/LSM™ gradients are prepared during this second centrifuge step. Since LSM™ is light sensitive, the bottles are prepared in a hood with the lights off. 180 mL of LSM™ ($\rho=1.0770-1.0800$ g/ml) is measured into each 400 ml bottle. 50 ml of isotonic Percoll™ ($\rho=1.07$ g/ml) is then layered onto the LSM™ by carefully pipetting the Percoll™ directly onto the LSM™. Experience has shown that better recoveries are had if there is a slight mixing of the Percoll®/LSM® interface. A sharp interface results in a dark red layer immediately below the PBMC which inhibits the migration of the granulocytes down the gradient. Complete mixing of the Percoll™ with the LSM™ is less efficient for isolating the PBMC. Elimination of Percol can be utilized with acceptable results. However, Percol adds robustness to the separation.

Once the bottles are prepared, the RB-1 ($\rho=1.04$ g/ml) is carefully layered onto each bottle with a peristaltic pump set at slowest speed. An experienced operator can increase the pump speed somewhat without disturbing the layers. After centrifugation for 45 minutes at 300 G (1030 rpm), the top layer is removed with a peristaltic pump with thin tubing (I.D. 3/16", O.D. 5/16", Wall 1/16") and discarded.

The second PBMC containing layer is collected, diluted at least five fold in PBS and centrifuged for 10 minutes at 500 G (1345 rpm). The cell pellet is resuspended in PBS in the original volume and the centrifuge repeated. The cells are then suspended in RPMI medium and combined in a two liter bottle. The bottle is placed on an orbital shaker until diluted and used in cell culture.

EXAMPLE 3

Culture of Peripheral Blood Mononuclear Cells

The cell concentrate from Example 2 is diluted to approximately $10^7$ cells/ml in RPMI medium. The RPMI is supplemented with 5.958 g/l HEPES, 2 g/l NaHCO$_3$, and 0.05% PF-68. 10 ml/l of 29.2 g/l glutamine and 200 IU/ml primer are added just before use. Cantell Interferon or concentrated interferon as produced in Example 6 or anion exchange purified interferon is added to the medium to prime the cells for interferon production. The cells are cultured at 37° C. in a spinner flask (about 100–150 rpm) in a water bath for about 2 hours. Then two Sendai virus particles per cell are added and the cells cultured for about two more hours. The viral particles should be sonicated just before use in order to disaggregate the particles. Alternatively, a bioreactor system may be employed.

Two hours after Sendai addition, the temperature of the water bath is dropped smoothly and slowly to 28° C. (this is done by adding ice over a period of 15 minutes) and the cells cultured for about 14 more hours. At the end of this period, the medium is harvested. If desired, the protease inhibitor Pefabloc™ or other similar protease inhibitors can be added 30 minutes before the end of culture at a final concentration of about 0.5 to about 5 mM. Pefabloc™ is kept as a 100X frozen aliquot at −70° C. A variety of suicide protease inhibitors have been tested for their ability to function in this regard, but Pefabloc™ provides almost complete inhibition and can be removed by size exclusion chromatography. A decoy substrate such as the peptide ala-ala-ala may be employed throughout the cell culture process.

EXAMPLE 4

Preparation of Sendai Virus Inducer

Although there are many inducers of interferon synthesis, this protocol uses Sendai virus that is purchased from SPAFAS, Inc. Storres, Connecticut which provides batches uniform in hemagglutination and interferon stimulatory activity. Because the virus is grown in the allantoic fluid of chicken eggs, the inducing virus contributes contaminating proteins to the culture which can later interfere with the purification of interferon. Therefore, it is preferred that the virus be purified by centrifugation on a 10% to 50% (w/w) density gradient of potassium tartrate before use. After centrifugation, the viral fractions arc isolated, concentrated and resuspended in PBS buffer. Other methods of purification are envisioned in accordance with techniques known in the art.

Specifically, the protocol requires thawing frozen virus at 37° C. with constant stirring. A clarifying centrifuge is performed to remove the feathers and red blood cells (Beckman J2-21 centrifuge with JCF-Z rotor). The clarified pool is held overnight at 4° C. (((Why?))) A 10–50% potassium tartrate gradient is established in Electronucleonics Model K centrifuge with Super G rotor. The clarified virus applied to the gradient and centrifuged for 18 hours at 100,000 G (a Beclukan L8-80 ultracentriftige with SW-28 swinging bucket rotor can be used for small preps). The gradient is eluted from the bottom of the tube and fractionated. The early peak (about 3/4 into the gradient) contains the viral particles. The particles are concentrated by centrifugation and resuspended in 1/100th the original crude volume with PBS.

EXAMPLE 5

Virus Inactivation

Culture media (CM, from example 3) is collected and the pH is dropped to pH 2.75 (range 2.0 to 3.0) with 1 M HCl. The acid should be added at a rate of about 5–20 ml/min with continuous mixing of the harvested CM. The acidified solution is stored at about 4° C. for 2 to 4 hours. Viral hemagglutination activity is eliminated in about thirty minutes or less with no detectable loss in interferon activity as measured by VSV assay. The pH of the CM is brought to about 4.40 (range 4.3 to 4.5) and the CM is prefiltered using a 0.45 pm filter (Millipak 200 Filter Unit (PIN: MPHL 20C A3)), followed by filtration with a 0.22 μm filter (Millipak 60 Filter Unit (P/N: MPGL 06G H2)) using a peristaltic pump. This system is capable of filtering about 7–10 liters before the pressure rises to 30–40 PSI and the 0.45 μm filter clogs.

EXAMPLE 6

Culture Media Capture Column Procedure

SP Sepharose Big Beads are strong ion exchangers with a large particle size (100–300 μm) which allows for high flow rates (1200–1800 cm/h) and quick absorltion. The ion exchange groups are coupled to the highly cross-linked agarose matrix through chemically stable ether bonds. The strong ion exchange groups maintain full protein binding capacity over the whole operating pH range (4–12). The primary objective of this procedure is to capture all the interferon in the media after culture and reduce the sample volume from about 10 liters to about 100 ml. This step is primarily for sample concentration and does little purification, although it removes the nutrients from the culture media and some small peptides. The specific procedure was as follows: Equipment: Bed Volume: 22 mm×100 mm (38 ml). Flow rate: Load and wash at 1579 cm/hr. Elute and clean at 474 cm/hr. Buffer: Sparged with helium or nitrogen. Column Temperature is about 4 to about 8 C. Detector: 280 nm. Fraction Collection: Sample is collected based on 280 nm absorbance, collection is started when absorbance begins to increase from baseline and stopped when absorbance returns to baseline.

Procedure: Dilute CM 1:1 with 40 mM sodium acetate, pH 4.4, on line as column is loaded (200CV). Use of a pH of 4.8 or higher can lead to loss of IFN (as measured by bioactivity assays, no loss is seen by ELISA). The column is washed with 20 mM sodium acetate, pH 4.4 (6CV). Elution is done in reverse with 1 M NaCl/100 mM Tris, pH 7.5 (8 CV). About 95% recovery is found in most cases.

Pefabloc™ can be added to the capture eluate immediately after elution to yield a concentration of 1 mM (23.94 mg/100 ml). This helps to inhibit any protease activity which may have concentrated with the IFN. The capture eluate is held for a maximum of about 20 minutes to one hour at room temperature before it is modified with Tween-20 and propylene glycol prior to being loaded onto the hydroxyapatite column. This protease inhibitor is optional, but may be desired where the eluate is to be stored for any length of time.

EXAMPLE 7

Hydroxyapatite Chromatography (HAC)

Ceramic hydroxyapatite (HA) chromatography (HAC) separates mixtures of biomolecules via adsorption at a biocompatible calcium/phosphate $[Ca_5(PO_4)_6(OH)_2]$ surface. The structural arrangement of the calcium and phosphate ions provides for adsorption of acidic, neutral and basic groups. Additionally, because the spatial arrangement of the functional groups is maintained in a rigid structure, HAC can accomplish separation of macromolecules by recognizing subtle structural differences between biomolecules. Because the support matrix also serves as the adsorbent, there are no chemically attached ligands to leach during the separation procedure. Ceramic HA can also be treated with 1 M NaOH, for effective cleaning and sterilization in one step.

HAC under the conditions described below removes about 98% of human serum albumin (HSA), which is a major interferon contaminant, and other contaminating proteins. Typical yields are between about 80±8% by bioassay and between about 75% and 85% by an interferon ELISA assay (an average of at least 6 runs). The procedure can be successfully scaled up to large volume preparations. The specific conditions for carrying out HAC are as follows:

Equipment: BioCad Chromatography Workstation or equivalent. Resin: Ceramic Hydroxyapatite, Type A, 40 μm, by American International Chemical, Inc. HAKS4 or its equivalent. Bed volume: approximately 1.5 ml of resin per liter of original culture medium ($10^7$ cell/ml) (e.g. 22 mm×100 mm=38 ml). Load level: a maximum of about 58 mg of total protein per ml of HA (as measured by the Pierce BCA assay of the culture medium (e.g., about 57 liters of original culture for 22 mm×100 mm 38 ml HAC column). Flow rate: Load and Wash at 720 cm³/hr. (Linear flow rate). Elute in reverse at about 360 cm³/hr. Buffers: are warmed to about 22°±3° C., about 0.2 μm filter sterilized and sparged with helium or nitrogen (except for 1 M NaOH and 1 M MES pH 6.5) for a minimum of about 30 minutes prior to use. Column temperature: about 22°±3° C. Detector: 280 nm. Fraction collection: during elution.

Procedure: A pool of crude interferon, such as the cation exchange capture is used for HAC. The capture pool is already at about 10% PG and 0.1% Tween-20, and is adjusted to a final pH of about 6.5±0.1 using about 2 M TRIS-Base, about pH 8.8. If the pH is exceeded, about 1 M MES, about pH 6.5 is used to adjust the pH down to about 6.5. Never shake or agitate the capture pool because of the potential to denature the product.

The crude interferon is applied to the HAC column. An initial wash of about 100 mM MES, about pH 6.5, about 200 mM NaCl, about 10% PG, about 0.1–0.5% Tween-20 (10CV) is followed by a drop to about pH 5.0 with about 50 mM NH₄OAc, about pH 5.0, about 10% PG, about 0.1–0.5% Tween-20 (linear gradient over 10CV). Once at about pH 5.0, the column is washed with about 50 mM NH₄OAc, about pH 5.0, about 10% PG, about 0.1–0.5% Tween-20 solution (5CV in forward direction, followed by 5CV in the reverse direction to reduce the volume of elution).

Elution of the partially purified interferon mixture is accomplished in reverse direction at about 360 cm³/hr using a step elution of about 50 mM Na₃PO₄, about pH 5.0, about 200 mM NaCl, about 10% PG (v/v), about 0.1–0.5% Tween-20 (10CV). This process yields a concentrated protein pool of a partially purified interferon mixture, which is preferred for the following size exclusion chromatography step. Using this HAC purification technique, approximately 98% of the human serum albumin (HSA) contaminant is removed as well as other contaminating proteins and peptides.

Alternatively, this initial wash can also be performed with about 10 mM TRIS-HCl, about pH 7.4, about 10% PG, and about 0.1% Tween-20. However, it is believed that when about 100 mM MES, about pH 6.5, about 200 mM NaCl, about 10% PG, about 0.1–0.5% Tween-20 is used for the initial wash, it provides a more purified intermediate. The load condition of about pH 6.5 (pH=6.5vs. pH=7.4) is believed to enhance the removal of calprotectin contaminant not removed at a higher load pH condition. It is preferable to use approximately 0.5% Tween-20 to improve resolution without adversely effecting recovery or purification.

Generally speaking, the manufactures of the HAC packing material typically recommend against the use of pH levels lower than 5.5. Quite surprisingly, however, it has been discovered that the use of lower pH levels greatly assists in the purification of the partially purified interferon product and that this lower pH of about 5.0 does not negatively impact the HAC column material.

To avoid stability problems, it is preferable to utilize the HAC eluate at least within about 2 days and more preferably within about 8 hours and most preferably within about 2 hours after elution. It should be understood that immediate use of the HAC eluate is recommended, i.e., within about two hours of elution, because of the possible appearance of a new peak in RP-HPLC after one week storage, although bioassay and ELISA indicate no change in the interferon when used immediately. When using immediately, HAC eluate is stored at about 4° C. to about 8° C. until loaded onto the SEC column to minimize proteolysis.

EXAMPLE 8

Size Exclusion Chromatography (SEC)

Superdex-75 prep grade is a highly resolving size exclusion media with average particle size of 34 $\mu$m. It is a composite of cross-linked agarose and dextran and is useful for the separation of proteins with molecular weights between approximately 3 kDa and 70 kDa. In a typical SEC performed as described below, higher molecular weight contaminants including HSA elute prior to the natural mixture of type I INF or interferon and lower molecular weight contaminants elute after the natural mixture of type I INF or interferon.

The first purification step, HAC, removes about 98% of the human serum albumin which is present in the crude material. It is essential that most, if not all, of the human serum albumin be removed early in the purification process because of its ability to bind to many chromatographic resins and also to the natural mixture of type I INF or interferon. Early attempts to remove human serum albumin under non-dissociating, non-denaturing conditions did not succeed. However, it has been quite surprisingly discovered that interferon subtype proteins associated with human serum albumin are separated by utilizing dissociating non-denaturing conditions.

Under dissociating, non-denaturing conditions (e.g. about 10% propylene glycol, about 0.01% Tween-20), a partially purified natural mixture of type I INF or interferon is successfully separated from the human serum albumin. Thus, it should be understood by those versed in this art that the use of dissociating, non-denaturing conditioned are critical in carrying out the present invention. A reference standard is not necessarily required prior to ruliming the SEC, and the HAC pool is loaded without any modification. Using this technique, only trace amounts of human serum albumin are found in the resulting interferon subtype eluate from the SEC. The major contaminants after SEC are believed to be thrombospondin 1-precursor fragment in the about 5–10 kDa region on SDS-PAGE gel. Purity assessment of the SEC pool by SDS-PAGE and coomassie stain is not preferred because of the preferential dye binding properties of the thrombospondin-1 precursor fragments. Purity by RP-HPLC is about 50% to about 80% or greater.

An increase in Tween-20 from about 0.01 to about 0.05% can be used to provide enhanced separation of a calprotectin dimer contaminant present, so that slightly better resolution is obtained. There is no difference seen between about 0.01% and about 0.05% Tween-20 in column performance and purity of final eluate pool. The specific conditions for the SEC step are as follows:

Equipment: A low pressure LC system (ISCO Proteam LC system 210 or equivalent) equipped with a UV detector operating at 280 nrn and a chart recorder or preferably an appropriate data handling system. Resin: Superdex by Phaimacia or its equivalent. Bed volume: 50 mm×955 mm (1850 ml). It should be understood that a column length of about 950 mm or greater is needed to obtain the appropriate resolution of interferon subtypes from contaminants. Load level: approximately 2 to 5% of Bed Volume and more preferably about 2.7% or less (i.e. 50.0 ml/1850 ml bed volume is optimal. Flow rate: about 3.0 ml/min. SEC buffer: about 50 mM Tris-HCl, about pH 7.4, about 10% propylene glycol, about 0.05% Tween-20 (Pierce Ultra Pure), about 50 mM NaCl, is sterile filtered at about 0.22 $\mu$m, stored at about 4° C. prior to use and sparged (helium or nitrogen) for about 30 minutes prior to run. Column temperature: about 4–8° C. Detector: UV at 280 nm. Fraction collection: A fraction collector was set to start at about 5.25 hours after the start of isocratic elution. Fractions of 2.5 min or 7.5 ml are collected and a total of 60 fractions are collected. Under these conditions, fractions 14–44 contain the natural mixture of type I INF or interferon.

Procedure: The HAC fraction is loaded onto the column without any modification via line B of the gradient former at about 3.0 ml/min. The separation is performed isocratically at about 3.0 ml/min and fractions 14–44 are collected. If desired, the SEC eluate can be stored at about –80° C. for up to about 1 week before continuing the purification process.

In the event that the SEC is reused for other batches, the following cleaning protocol can be used for cleaning the SEC system: 1CV of about 0.5 N NaOH is run through the column at about 20 cm/hr. 1CV of about 1 M TRIS-HCl (at about pH 7.4) is run through the column at about 20 cm/hr. 2CV of SEC running buffer at about 20 cm/hr. At the end of the cleaning procedure, the pH of the effluent buffer should be at about pH 7.4.

EXAMPLE 9

Anion Exchange (AX) Chromatography

Anion exchange (AX) is suitable as a step for purifying IFNs from contaminating proteins due to the acidic nature of the interferons (pI<7.0). Using Tris buffer at pH 7.5, natural IFNs carry a net negative charge (except for IFN-$\omega$) and can be eluted and purified using a competing ion such as chloride. The AX resin, Source-30Q, Pharmacia, or its equivalent, uses quaternary amino groups and is appropriate for this application because of its wide pH stability, temperature, and flow rate ranges (pH 2–12, 4–40° C. 300–1000 cm/lir). In this method, the partially purified interferon mixture obtained from SEC is adsorbed onto the 30Q matrix at low ionic strength and the interferon proteins are eluted in the reverse order of their acidity. This can be accomplished for example by a linear gradient with a competing ion such as Cl$^-$or a 70 column volume wash with a buffer (about 50 mM Tris-HCl, about pH 7.5, about 0.05% Tween-20) followed by a step elution with 50 mM Tris, 0.01% Tween-20, 200 nM NaCl, pH 7.5. The purity of the AX eluate averaged between about 95% to about 98% as measured by densitometric analysis of reducing and non-reducing SDS-PAGE and with RP-HPLC. Purity obtained is between about 95% and about 98%, as measured by RP-HPLC. Recovery averaged about 60% to about 70% as measured by anti-viral bioassay and interferon ELISA. However, IFN-ω, IFN-α21 and IFN-α14 subtypes are greatly reduced. A minor amount of unidentified low molecular weight contaminants remain. It is believed that these are IFN fragments. Specifically, the procedure was as follows:

Equipment: Alta Explorer™ chromatography work station or its equivalent with Frac-900™ fraction collector or its equivalent. Resin: Source-30Q™ from Pharmacia Biotech, product number 17–1275, or equivalent. Bed Volume: 7.5 mm×50 mM Altech PEEK column with 2.21 ml bed volume. Flow rate: Load at about 722 cm/hr. Wash and elute at 361 cm/hr. Load: 1 mg protein/ml of bed volume. A lower load may slightly improve the recovery of interferon subtypes, but will increase the column size and subsequent elution volume. Injection volume is variable. Buffers: Equilibration and elution buffers are filtered through a C-18 RPLC column and vacuum filtered through sterile 0.22 μm cellulose acetate filter prior to adding Tween-20. All buffers are sparged with helium or nitrogen prior to and during each AX run. Column temperature: ambient about 20–25° C. Detector: dual wavelength, 254 nm and 280 nm. Fraction collection: 3 ml fractions are collected when elution begins.

Procedure: The SEC pool of IFN is diluted 1:1 with deionized water, bringing the salt concentration to about 25 mM, the pH is checked to ensure that it is at about 7.4 and the SEC pool is applied to the 30Q column. Some loss of interferon occurs in the flow through (11–23% by ELISA and bioassay). The nature of this loss is not fully understood, but it is probably due to loss the IFN-ω, IFN-α14 and IFN-α21 which may not bind to the Source-30Q resin because of their isoelectric points. This column is washed with about 10–70 CV of about 50 mM Tris-HCl, about pH 7.5, about 0.05% Tween-20. This wash removes the main contaminants which are thrombospondin- 1 -precursor protein fragments and IL-6 and other low molecular weight peptides. Elution is carried out via a linear gradient of 0 to about 200 mM NaCl, about 50 mM Tris-HCl, about pH 7.5, about 0.05% Tween-20 (60 CV) or more preferably, a step elution using about 200 mM NaCl, about 50 M Tris-HCl, about pH 7.5, about 0.01% Tween 20. In the case of gradient elution, fractions 4–40 are pooled to provide maximum interferon subtype recovery, but fractions 16–38 are pooled to provide maximum purity.

Due to the small amount of resin required for each batch, the used resin can be discarded after each run, eliminating the need for cleaning and sterilization, thereby reducing overall procedural costs and time.

Currently, it is not recommended that this AX purified natural mixture of type I INF or interferon be subjected to repeated freeze thaw, as this seems to cause changes in the intensity of the RP-HPLC peaks, although no loss of activity is seen by ELISA.

This AX procedure generates an acceptable bulk intermediate natural mixture of type I INF or interferon in accordance with the present invention which is suitable for pharmaceutical formulation and fill.

EXAMPLE 10

Hydrophobic Interaction Chromatography (HIC)

An alternative to the AX procedure, hydrophobic interaction chromatography (HIC) may be employed. HIC, like reversed phase chromatography, is a technique for separating biomolecules by their degree of hydrophobicity. Since the elution of proteins in HIC uses a decreasing salt gradient, the biological activity of the eluted proteins is usually preserved. There are many different types of HIC resins; however, the natural mixture of type I INF or interferon is found to have the best separation from contaminants using a weakly hydrophobic propyl ligand with a silica matrix, such as Bakerbond Wide Pore HI-propyl (40 μm), JT Baker L05082 or L05083 or equivalents. This resin offers a high binding capacity along with the necessary rigidity to withstand high flow rates for quick and consistent processing. Due to the small amount of resin required for each batch, the used resin can be discarded after each run, eliminating the need for cleaning and sterilization thereby reducing overall procedural costs and time.

The HIC method described herein uses a high concentration of a non-chaotropic salt to bind the IFN subtypes to the HIC column. It is believed that the non-chaotropic salt has a stabilizing influence on the interferon subtype structures. Because the resin is silica based, it is coated by JT Baker with polyimines for bioprocessing use to prevent non-specific irreversible absorption of proteins to the resin. Phosphate buffer and sodium chloride are used to elute the natural mixture of type I INF or interferon. The use of this combination of phosphate buffer and sodium chloride eliminates the need for an additional buffer exchange step after the elution. Because of the ionic nature of the resin backbone imparted by the polyimine coating, it was found necessary to drop the pH of the elution buffer to about 2.2 to obtain complete recovery of the natural mixture of type I INF or interferon. A variable loss (up to about 25%) of the IFN-α1 is observed during the washing of the column. This is currently not understood. Specifically, the procedure is as follows:

Equipment: a BioCad Chromatography Workstation or equivalent. Resin: Bakerbond Wide Pore HI-propyl (40 μm) JT Baker L05082 or L23083 or equivalent. Bed Volume: 16 mm×10 mm (2.01 ml). Load: HI Propyl binding capacity for natural mixture of type I INF or interferon has not yet been determined. However, the stated literature breakthrough for HI-Propyl is about 150–200mg protein/gm for a column of standard size (2 ml; 0.67 gm). Thus, a 2 ml column should be sufficient to bind the approximate 35 mg of load (with 15–20 mg of contaminant being in the FT/Wash) derived from a 30 liter original culture. Flow Rate: all at about 8.04 ml/min (240 cm/hr). Buffer: All buffers are sparged with helium or nitrogen for about 30 minutes prior to use. Column temperature: ambient 20–25° C. Detector: UV at about 280 nm. Fraction collection during the elution.

Procedure: The IFN-containing SEC fractions are applied to the HI-Propyl resin with in-line mixing (1:1.6) with about 2 M $(NH_4)_2SO_4$ (final salt concentration at about 1.25 M) followed by a 1.25 M $(NH_4)_2SO_4$ 25, mM Tris, pH 7.4 wash (10 CV) allows full binding of the all IFN subtypes. If inline mixing is not possible, the salt can be slowly added directly to the SEC pool to a concentration of about 1.25M $(NH_4)_2SO_4$. The composition of the mobile phase is then changed from about 25 mM TRIS, about pH 7.4, about 1.25 M $(NH_4)_2SO_4$ to about 25mM $Na_3PO_4$, about pH 7.0, about 1.75 M NaCl through a linear gradient (10 CV). The column is washed with about 25 mM $Na_3PO_4$, about pH 7.0, about 1.75 M NaCl (60 CV) in order to wash off any residual $(NH_4)_2SO_4$.

The natural mixture of type I INF or interferon is eluted from the column with a 5 column volume linear gradient from about 25 mM $Na_3PO_4$, about pH 7.0, about 1.75 M NaCl to about 25 mM Na$_3$PO$_4$, about pH 7.0. At low ionic strength of the mobile phase, some of the subtypes of the natural mixture of type I INF or interferon remain bound. In order to elute the remaining natural mixture of Type I INF or interferon, the pH of the mobile phase is lowered to a final pH of approximately 2.2 using about 42.5 CV of about 0.01 M HCl. After the low pH elution, the salt drop and pH drop fractions are combined to form a final pool which has a buffer composition of approximately: about 450 mM NaCl, about 2–3 mM Na$_3$PO$_4$, about pH 6.4–6.6. This method is reproducible and scalable with full subtype retention and high mass recovery (about 65% by anti-viral ELISA, about 67% by bioassay and about 75–80% by RP-HPLC). The bioactivity is also retained with a purity level of greater than 95% by both RP-HPLC and reducing and non-reducing SDS-PAGE using coomassie equilibrium staining. An independent laboratory has confirmed that the ammonium sulphate present in the final product was at background level and experiments have shown that the HIC eluate is stable to repeated freeze thaw cycles.

EXAMPLE 11

Characterization of Purified Interferon

The natural mixture of interferon was characterized in several ways at each step in the procedure. Characterizations included protease assay (Universal Protease Assay, Boehringer Mannhein), BCA assay for total protein (Pierce, RD0125), ELISA for interferon omega (ω) (Bender Wein, Austria), ELISA for IFN-α (Endogen, Pestka Biomedical Laboratories, BioSource International or Bender MedSystems), ELISA for IL-6 (CYT Immune, Inc., MD), reducing and non-reducing SDS-PAEE with coomassie (equilibration staining), silver staining or Western blot followed by densitometric analysis, antiviral bioassay, RP-HPLC, and amino terminal and tryptic fragments sequencing (with BioBrene.TFA filter) and mass spectrometry of individual RP-HPLC peaks. Summaries of the data obtained is provided as follows:

TABLE 1

COMPARISON OF PURIFICATION METHODS

| | HAC | /SEC | AX | HIC |
|---|---|---|---|---|
| Purity: Reducing SDS-PAGE | NA | NA | 95–98% | 95–98% |
| Purity: Non-reducing SDS-PAGE | NA | NA | 96.4% | 98.7% |
| Purity: RP-HPLC | NA | about 50% | ≥95 | ≥95% |
| Yield: ELISA for IFN-α | 81.1 ± 2.9% | 93.7 ± 12.8% | 58 ± 3.6% | 69.8 ± 5.5% |
| Yield: ELISA for IFN-ω | NA | NA | 1% | 89.4 ± 5.7% |
| Yield: Bioassay | 71.7 ± 18% | 97% ((>70%?)) | 59.6 ± 13.8% | 69.8 ± 11.7 |
| Yield: RP-HPLC | NA | NA | NA | NA |
| Stability to Freeze/Thaw | ND | ND | No | Yes |

EXAMPLE 12

RP-HPLC of Natural Mixtures of Type I IFN or Interferon Formulated with 1 mg/ml HSA Currently, only RP-HPLC and CE have enough resolution to detect any changes in the primary structure of a protein. Primary structure changes (e.g. deamidation, Met-oxidation, or C-terminal truncation, internal cleavage) are considered the formation of new protein species and must be monitored in the formulated product. However, the final formulated NATURAL MIXTURES OF TYPE I IFN OR INTERFERON™ product contains a 20–40 fold excess of HSA, which is sufficient to mask the interferon signals. Therefore, the standard prior art RP-HPLC methods for analyzing the intermediate interferon products cannot be used with the formulated NATURAL MIXTURES OF TYPE I IFN OR INTERFERON™ without losing resolution and reproducibility.

An RP-HPLC method has been successfully developed which can be used to analyze interferon samples containing up to 1 mg/ml of HSA. Specifically the procedure is as follows:

EQUIPMENT Gradient HPLC: Beckman Solvent System Gold Nouveau or equivalent. Column: Vydac C18 protein & peptide, 4.6 mm×25 cm (Vydac 218TP54) or equivalent. Detector: Beckman System Gold 166/168 or equivalent UV. Data handling software: Beckman Gold Nouveau or equivalent. Autosampler: Beckman System Gold 507e with 1 mL Rheodyne PEEK sample loop or equivalent.

SOLUTIONS Mobile Phase A: (0.1% TFA/H$_2$O). Measure out 1 liter of HPLC grade H$_2$O (Fisher W5–4). Add 1.0 ml TFA under the fume hood (Sequencing grade PE-Applied Biosystenis Division 400003). Mix thoroughly, filter using 0.45 μm nylon filter and store in glass bottle until use. Sparge with helium for approximately 15–30 minutes prior to running method. Mobile Phase B (0.085% TFA/5% H$_2$O/95% Acetonitrile. Measure out 950 ml of HPLC grade acetonitrile (Fisher A998-4). Add 50 ml of HPLC grade H$_2$O. Add 850 μl of TFA. Mix thoroughly, filter using 0.45 μm nylon filter and store in glass bottle until use. Sparge with helium for approximately 15–30 minutes prior to use. 50% Methanol/50% H$_2$O Measure out 500 ml of HPLC grade H$_2$O. Add 500 ml of HPLC grade methanol. Mix thoroughly, filter using 0.45 μm nylon filter and store in glass bottle until use.

SAMPLE PREPARATION Begin with 5.0×10$^6$ IU/ml/1.0 mg/ml HSA NATURAL MIXTURES OF TYPE I IFN OR INTERFERON™ formulated product. Aliquot 1 ml of NATURAL MIXTURES OF TYPE I IFN OR INTERFERON™ into a wide-mouth amber autosampler vial. Add 667 μl of Mobile Phase B. Cap vial with appropriate septa (acetonitrile resistant, e.g. PTFE liner) and invert several times to insure adequate mixing. Place samples in a chilled (4° C.) autosampler prior to run. (Note: The final volume of prepared sample (1667 μl) should be adequate for a 999 μl sample injection. Always prepare the additional volume of sample since autosampler requires more than the actual injected volume for analysis.)

OPERATING CONDITIONS Flow rate: 1.0 ml/min. Column: Vydac C-18 protein & peptide, 4.6 mm×25 cm (Vydak 218tp54 or equivalent). Injection Volume: 1.0 ml. Detection: UV at 214 nm. Equilibration: 40% Buffer B. Column temperature: Ambient (20–25° C.). Autosampler tray temp: 4° C. Pressure: upper limit; 6.00 KPSI, lower limit; 0.05 KPSI. Procedure: Gradient:

| Line | Time (min) | Module | Function | Value | Duration |
|---|---|---|---|---|---|
| 1 | 0.00 | DET 166 | Auto zero | • | • |
| 2 | 0.00 | Pumps % B | | 40.00 | 5.00 |
| 3 | 5.00 | Pumps % B | | 45.00 | 7.50 |
| 4 | 12.50 | Pumps % B | | 45.00 | 7.50 |
| 5 | 20.00 | Pumps % B | | 55.00 | 30.00* |
| 6 | 50.00 | Pumps % B | | 90.00 | 2.50 |

-continued

| Line | Time (min) | Module | Function | Value | Duration |
|------|------------|--------|----------|-------|----------|
| 7 | 52.50 | Pumps % B | | 40.00 | 2.50 |
| 8 | 55.00 | Pumps % B | | 40.00 | 5.00 |
| 9 | 60.00 | Pumps Flow rate | | 0.00 | 0.00 |
| 10 | 60.00 | DET 166 | Stop Data | • | • |
| 11 | 60.00 | SystemEnd Run | | • | • |

*0.33% B/min gradient
One might extend the wash at 45% B from 7.5 min to 15 min in order to minimize the HSA overlap into the natural mixtures of Type I IFN or region.

The final parameters for the method was derived from experiments which tested the effect of increasing amounts of acetonitrile on the binding of HSA to C-18 resin. This titration experiment was performed using increasing amounts of acetonitrile in the load and monitored for the loss of interferon proteins. The final acetonitrile concentration of 40% was chosen to give the optimum removal of TISA without losing the interferon proteins. It is important to note that at 42% acetonitrile, much of the IFN-α14 was lost. With less than 40% acetonitrile, HSA produced extraneous protein peaks in the IFN region. Therefore, precise composition of acetonitrile (40%) must be exercised when preparing samples for analysis.

Natural mixture of Type I IFN or interferon with and without HSA gave the same elution profile when loaded at 40% acetonitrile. This indicates that very little if any of natural mixture of Type I IFN or interferon is being carried through along with HSA, which is in a 20–40 fold in excess over the interferon concentration. The results of multiple chromatograms give an indication of the excellent reproducibility attained when injecting the same sample 8 times (not shown). Reproducibility is also shown using multiple samples at T=0 in a stability study.

Therefore, the RP-HPLC method for HAS formulated of natural mixture of Type I IFN or interferon provides a tool for the determination of any primary structural changes which may occur over time. The method is reproducible and yields excellent resolution of all subtypes present in the final interferon mixture.

This method can also be used to analyze products from different vendors currently being formulated with HSA. The method performed well when analyzing Interferon Sciences material Alferon™. This method confirms the claimed Alferon subtypes such as IFN-α2, IFN-α8. Since we have not confirmed the presence of IFN-α7, we cannot comment on this subtype.

RP-HPLC can be used as a "physical measurement" (e.g. the presence or absence of a compound), but not to determine biological activity of a compound. RP-HPLC of natural mixture of Type I IFN or interferon when compared to a T=0 analysis can be used to indicate primary structural changes which may occur in the natural mixture of Type I IFN or interferon product over time (e.g. deamidation, Met-oxidation, C-terminal truncation or internal cleavage). It is important to keep in mind that a primary structural change may or may not result in a conformational change. However, a change in the RP-HPLC chromatogram is indicative of a conformational or structural change in the protein undergoing analysis. Primary structural changes as well as conformational changes in one or more of natural mixture of Type I IFN or interferon subtypes may or may not result in a change in bioactivity. RP-HPLC should be used in conjunction with mass spectroscopy for final determination of any structural changes that may occur over time. In the case of the final formulated natural mixture of Type I IFN or interferon product, RP-HPLC is to be used both as a qualitative tool, e.g. shift in retention time, and semi-quantitative tool, e.g. relative peak height/area with respect to T=0.

The above RP-HPLC can be modified to allow the incorporation of internal and external standards in order to monitor column performance. Several standards have been evaluated, and it has been discovered that phenylthiohydantoin norleucine (PTH-Nle, SIGMA P1877) is a satisfactory internal standard. 25 mg is mixed with 10 ml of Mobile phase B and stored at −20° C. The solution is good for 6 months. It is freshly diluted and used at 25 μg/ml as an internal standard where it elutes at about 10.5 minutes into the run and should have an O.D. of about 0.5 AU. Increasing the wash interval at 40%B results in the separation of the HSA into two peaks. This interval between the two peaks was ideal for the incorporation of PTH-Nle as an internal standard.

N-fluorenylmethoxycarbonyl L norleucinie (Fmoc-Nle, SIGMA F 2917) is used as an external standard. 10 mg of Fmoc-Nle is weighed into a flask with 5 ml of 40% Mobile phase A/60% Mobile phase B and warmed until solubilized. Then the volume is brought to 10 ml with 40% Mobile phase A/60% Mobile phase B. The solution is stored at −20° C. and is good for 6 months. It is freshly diluted and used at 5 μg/ml as an external standard where it elutes at about 30.0 minutes and should have an O.D. of about 0.55 AU.

EXAMPLE 13

Natural Mixtures of Type I IFN or Interferon™ Formulations: Tris/PBS/N$_2$

Experiments are performed with natural mixture of Type I IFN or interferon formulated with 1 mg/ml HSA in 100% Tris-HCl, pH 7.4 at 22° C., 50 mM NaCl, 0.01% Tween-20 or 1 mg/ml HSA in 50% Tris-HCl, pH 7.4 at 22° C., 50 mM NaCl, 0.01% Tween-20 and 50% PBS, pH 7.4 at 22° C., 0.01% Tween-20. The samples were stored at 40° C. in silanized vials that were plus or minus covered with a layer of N$_2$ and assayed over a one month period (0, 2, 4, 7, 9, 11, 14 and 28 days). Assay was by RP-HPLC with the internal standards described above, and ELISA and bioassay. Autosampler vials were weighed before and after sample injection to account for sample injection variances.

There does not appear to be any change in the RP-HPLC profile shape, indicating no changes in the primary structure of natural mixture of Type I IFN or interferon at 40° C. over a 4 week period. Based upon the foregoing, it should now be apparent that the highly purified natural mixtures of Type I INF or interferon and methods and uses described herein will carry out the objectives of the instant invention. Thus, the present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

Having described our invention, we claim:

1. A method of producing interferon, said method comprising:
   a) subjecting a fluid containing a plurality of leukocytes to density gradient centrifugation and collecting a buffy coat therefrom,
   b) maintaining the temperature of the buffy coat at a constant 22°±3° C. with sufficient oxygenation to retain cell viability of the buffy coat until use, c) purifying the buffy coat by density gradient centrifugation and without using a lytic agent, and d) collecting a preparation of at least 10% monocytes (v/v) with less than 10% granulocytes (v/v) from an interface created by the density gradient maintaining the monocytes;

e) culturing said preparation of at least 10% monocytes (v/v) with at least a stimulus to produce a crude interferon, f) concentrating the crude interferon to remove low-molecular weight contaminants and liquid volume to produce a concentrated crude interferon by removing a resulting supernatant, g) removing an amount of serum albumin and other contaminants from the concentrated crude interferon to produce a partially purified interferon mixture containing a plurality of subtypes by using ion exchange chromatography, h) removing further remaining serum albumin and other contaminants from the partially purified interferon mixture to generate an interferon mixture having a purity of between about 50% and about 80% (w/w) by using hydroxyapetite chromatography, and i) purifying the about 50% to about 80% interferon (w/w) mixture by a third purification means selected from a group consisting of at least size exclusion chromatography and anion exchange chromatography to produce a highly purified mixture of Type I interferon having a purity of at least about 95% (w/w) and containing no more than about 35% by weight IFNα-2 and IFNα-8 subtypes.

2. A method of producing interferon, said method comprising:

a) subjecting a fluid containing a plurality of leukocytes to density gradient centrifugation and collecting a buffy coat therefrom, b) maintaining the temperature of the buffy coat at a constant 22°±3° C. with sufficient oxygenation to retain cell viability of the buffy coat until use, c) purifying the buffy coat by density gradient centrifugation and without using a lytic agent, d) collecting a preparation of at least 10% monocytes (v/v) with less than 10% granulocytes (v/v) from an interface created by the density gradient maintaining the monocytes;

e) culturing said preparation of at least 10% monocytes (v/v) with at least a stimulus to produce a crude interferon, f) concentrating the crude interferon to remove low-molecular weight contaminants and liquid volume to produce a concentrated crude interferon by removing a resulting supernatant, g) removing an amount of serum albumin and other contaminants from the concentrated crude interferon to produce a partially purified interferon mixture containing a plurality of subtypes by a first purification means consisting of cation exchange chromatography, h) removing further remaining serum albumin and other contaminants from the partially purified interferon mixture to generate an interferon mixture having a purity of between about 50% and about 80% (w/w) by a second purification means consisting of hydroxyapetite chromatography and size exclusion chromatography, and i) purifying the about 50% to about 80% interferon (w/w) mixture by a third purification means selected from a group consisting of anion exchange and size exclusion chromatography to produce a highly purified mixture of Type I interferon having a purity of at least about 95% and containing an IFNω subtype and no more than about 35% by weight IFNα-2 and IFNα-8 subtypes.

3. A method of producing interferon, said method comprising:

a) subjecting a fluid containing a plurality of leukocytes to density gradient centrifugation and collecting a buffy coat therefrom, b) maintaining the temperature of the buffy coat at a constant 22°±3° C. with sufficient oxygenation to retain cell viability of the buffy coat until use, c) purifying the buffy coat by density gradient centrifugation and without using a lytic agent, d) collecting a preparation of at least 10% monocytes (v/v) with less than 10% granulocytes (v/v) from an interface created by the density gradient maintaining the monocytes;

e) culturing said preparation of at least 10% monocytes (v/v) with at least a stimulus to produce a crude interferon, f) concentrating the crude interferon to remove low-molecular weight contaminants and liquid volume to produce a concentrated crude interferon by removing a resulting supernatant, g) removing an amount of serum albumin and other contaminants from the concentrated crude interferon to produce a partially purified interferon mixture containing a plurality of subtypes by a first purification means consisting of cation exchange chromatography, h) removing further remaining serum albumin and other contaminants from the partially purified interferon mixture to generate an interferon mixture having a purity of between about 50% and about 80% (w/w) by a second purification means consisting of hydroxyapetite chromatography, and i) purifying the about 50% to about 80% interferon (w/w) mixture by a third purification means selected from size exclusion chromatography and anion exchange chromatography to produce a highly purified mixture of Type I interferon having a purity of at least about 95% and containing IFNα-1, IFNα-2, IFNα-5, IFNα-7, IFNα-8, IFNα-10, IFNα-14, IFNα-21, and IFNω subtypes.

4. A method of producing interferon, said method comprising:

a) subjecting a fluid containing a plurality of leukocytes to density gradient centrifugation and collecting a buffy coat therefrom, b) maintaining the temperature of the buffy coat at a constant 22°±3° C. with sufficient oxygenation to retain cell viability of the buffy coat until use, c) purifying the buffy coat by density gradient centrifugation and without using a lytic agent, d) collecting a preparation of at least 10% monocytes (v/v) with less than 10% granulocytes (v/v) from an interface created by the density gradient maintaining the monocytes;

e) culturing said preparation of at least 10% monocytes (v/v) with at least a stimulus to produce a crude interferon, f) concentrating the crude interferon to remove low-molecular weight contaminants and liquid volume to produce a concentrated crude interferon by removing a resulting supernatant, g) removing an amount of serum albumin and other contaminants from the concentrated crude interferon to produce a partially purified interferon mixture containing a plurality of subtypes by a first purification means consisting of cation exchange chromatography, h) removing further remaining serum albumin and other contaminants from the partially purified interferon mixture to generate an interferon mixture having a purity of between about 50% and about 80% (w/w) by a second purification means consisting of hydroxyapetite chromatography, and i) purifying the about 50% to about 80% interferon (w/w) mixture by a third purification means selected from a group consisting of size exclusion chromatography and anion exchange chromatography to produce a highly purified mixture of Type I interferon having a purity of at least about 95% and containing IFNα-1, IFNα-2, IFNα-5, IFNα-7, IFNα-8, IFNα-10, IFNα-14, IFNα-21 subtypes, and IFN-ω.

5. A method of interferon production, said method comprising:

a) subjecting a fluid containing a plurality of leukocytes to density gradient centrifugation and collecting a buffy coat therefrom, b) maintaining the temperature of the buffy coat at a constant 22°±3° C. with sufficient oxygenation in a gas permeable container to retain cell viability of the buffy coat until use, c) purifying the buffy coat by density gradient centrifugation and without using a lytic agent, d) collecting a preparation of at least 10% monocytes (v/v) with less than 10% granulocytes (v/v) by using a peristaltic pump, e) culturing said preparation of at least 10% monocytes (v/v) with a Sendai virus to produce a crude interferon, f) concentrating the crude interferon to remove low-molecular weight contaminants and liquid volume to produce a concentrated crude interferon by removing a resulting supernatant, g) removing an amount of serum albumin and other contaminants from the concentrated crude interferon to produce a partially purified interferon mixture containing a plurality of subtypes by using ion exchange chromatography, h) removing remaining serum albumin and other contaminants from the partially purified interferon mixture to generate an interferon mixture having a purity of between about 50% and about 80% (w/w) by hydroxyapetite chromatography and size exclusion chromatography, and i) purifying the about 50% to about 80% interferon (w/w) mixture by a third purification means selected from a group consisting of size exclusion chromatography and anion exchange chromatography to produce a highly purified mixture of Type I interferon having a purity of at least about 95% and containing IFNα-1, IFNα-2, IFNα-5, IFNα-7, IFNα-8, IFNα-10, IFNα-14, IFNα-21, and IFN omega subtypes.

* * * * *